(12) United States Patent
Seitz et al.

(10) Patent No.: US 6,450,997 B1
(45) Date of Patent: Sep. 17, 2002

(54) ABSORBENT ARTICLES HAVING A BELLOWS FOR CIRCULATING FRESH AIR

(75) Inventors: Bret Darren Seitz, West Chester, OH (US); Jay Anthony Krebs, Edgewood, KY (US)

(73) Assignee: The Procter & Gamble Company, Cincinnati, OH (US)

(*) Notice: Subject to any disclaimer, the term of this patent is extended or adjusted under 35 U.S.C. 154(b) by 14 days.

(21) Appl. No.: 09/599,713

(22) Filed: Jun. 21, 2000

(51) Int. Cl.[7] .................................................. A61F 13/15
(52) U.S. Cl. .................................. 604/385.01; 604/558
(58) Field of Search ........................... 604/385.01, 358, 604/373, 378, 367

(56) References Cited

U.S. PATENT DOCUMENTS

| | | | |
|---|---|---|---|
| 4,887,602 A | 12/1989 | O'Leary | 604/305.1 |
| 5,582,604 A | 12/1996 | Ahr et al. | 604/385.1 |
| 5,643,241 A | 7/1997 | Ahr et al. | 604/385.1 |
| 5,649,920 A | 7/1997 | Lavon et al. | 604/385.2 |
| 6,280,426 B1 * | 8/2001 | Turner | 604/378 |

FOREIGN PATENT DOCUMENTS

| | | | |
|---|---|---|---|
| CA | 2276303 | 11/2000 | A61F/13/15 |
| WO | WO 01/15648 A1 | 3/2001 | |

* cited by examiner

Primary Examiner—Amy Vanatta
Assistant Examiner—Angela J. Grayson
(74) Attorney, Agent, or Firm—Jay A. Krebs; David M. Weirich; Ken K. Patel

(57) ABSTRACT

An absorbent article having a repeatably deformable bellows to force airflow through the absorbent article. The bellows expands and contracts, utilizing biomechanical motion of the wearer to draw air into a bellows chamber at one end and to expel the air out of the bellows chamber at a separate end. The airflow assists in drying the skin of the wearer which is damp as a result of perspiration or evaporation of urinary waist absorbed by the core.

6 Claims, 9 Drawing Sheets

ABSORBENT ARTICLES HAVING A BELLOWS FOR CIRCULATING FRESH AIR

FIELD OF THE INVENTION

The present invention is related to absorbent articles having an inflatable component that is repeatably deformable for providing the circulation of fresh air about the absorbent article.

BACKGROUND OF THE INVENTION

Absorbent articles for personal care products such as diapers, adult incontinence articles, wipes and feminine hygiene products are widely used consumer products. The large demand for such products has inspired manufacturers to provide improved versions of the products and their methods of manufacture. For instance, the major function of diapers and adult incontinence briefs is to prevent bodily waste from soiling, wetting, or otherwise contaminating clothing or other articles, such as bedding, that come in contact with the wearer. In recent years, disposable diapers, such as those disclosed in U.S. Pat. No. 3,860,003 issued to Kenneth Barclay Buell on Jan. 14, 1975, incorporated herein by reference, have become very popular with the public and have generally replaced durable cloth absorbent articles because of their convenience and reliability. However, despite the effectiveness of such disposable absorbent articles, bodily wastes often are stored in the diaper such that the wastes soil and/or irritate the skin of the wearer. Thus, the search has continued for even more effective devices.

In the past, considerable effort has been made to increase the comfort of absorbent articles such as infant diapers or adult incontinent pads by making a wet product feel dryer to the wearer. This has been accomplished by the use of relatively hydrophobic nonwoven fabric as the topsheet of the product. By maintaining the skin as dry as possible the growth of ammonia liberating bacteria on the skin can be reduced which in turn reduces irritation due to ammonia caused diaper rash.

It is commonly accepted that diaper climate (e.g. temperature and relative dampness, rash) and comfort. Although hydrophobic nonwoven inner layers have been effective in making a wet fabric feel dryer, evaporation from a loaded diaper core through the topsheet results in a high relative humidity inside the space between the topsheet and the wearer's skin, contributing to skin dampness and rash associated therewith. Thus, reducing the relative humidity inside the space between the topsheet and the wearer's skin can reduce skin dampness and the consequential rash resulting therefrom.

In addition to reducing skin dampness, the wearer's comfort may be improved by cooling the skin inside the diaper. By moving air through gaps formed between the diaper and the wearer's skin, the coefficient of convective heat transfer can be increased and effectively lower the temperature of the skin.

Accordingly, it is desirable to provide an absorbent article, such as a diaper, that can effectively reduce the relative humidity and cool the skin inside the article when worn by the wearer. The present invention provides an absorbent article incorporating an air moving device which forces fresh air through the article when worn by the wearer, lowering the relative humidity and cooling the skin inside the article.

SUMMARY OF THE INVENTION

The present invention is an absorbent article, such as a diaper, comprising a backsheet, a topsheet, an absorbent core disposed intermediate the backsheet and the topsheet and a bellows which is repeatably deformable to force airflow through the absorbent article in a controlled manner. The bellows expands and contracts, utilizing biomechanical motion of the wearer, such as expansion and contraction of the abdomen during normal breathing or normal motion such as bending or leg motion, to draw fresh air into the bellows at one end and to expel the air out of the bellows and into the article at a separate end. The airflow assists in drying and cooling the skin of the wearer which is damp as a result of perspiration induced by elevated temperature and/or high relative humidity associated with evaporation from a loaded absorbent core.

In a preferred embodiment, the bellows comprises a first, body facing side, a second side opposite the body facing side, an upper end and a lower end, wherein the upper end has an inlet port disposed therein to draw fresh air into the bellows and the lower end has an outlet port to expel air out of the bellows. Both the inlet and outlet ports include one-way flaps, providing a unidirectional flow of air entering the inlet ports as well as a unidirectional flow of air exiting the outlet ports. The bellows may be disposed intermediate the topsheet and the absorbent core with the second side attached to the absorbent core or conversely, with the body facing side attached to the topsheet.

In one embodiment, the bellows includes an inflatable air accumulator attached to the outlet port of the bellows. The air accumulator has a body facing side with a plurality of apertures disposed therein forming a cumulative flow area. Once inflated by the bellows, the air accumulator provides for a gradual, generally continuous airflow exiting the plurality of apertures and flowing towards the skin of the wearer.

BRIEF DESCRIPTION OF THE DRAWINGS

These and other features, aspects and advantages of the present invention will become better understood with regard to the following description, claims, and accompanying drawings where:

FIG. 6b is a cross sectional view of the bellows illustrated in FIG. 6a.

FIG. 7b is a cross sectional view of the bellows depicted in FIG. 7a.

DETAILED DESCRIPTION OF THE INVENTION

Figure 1:
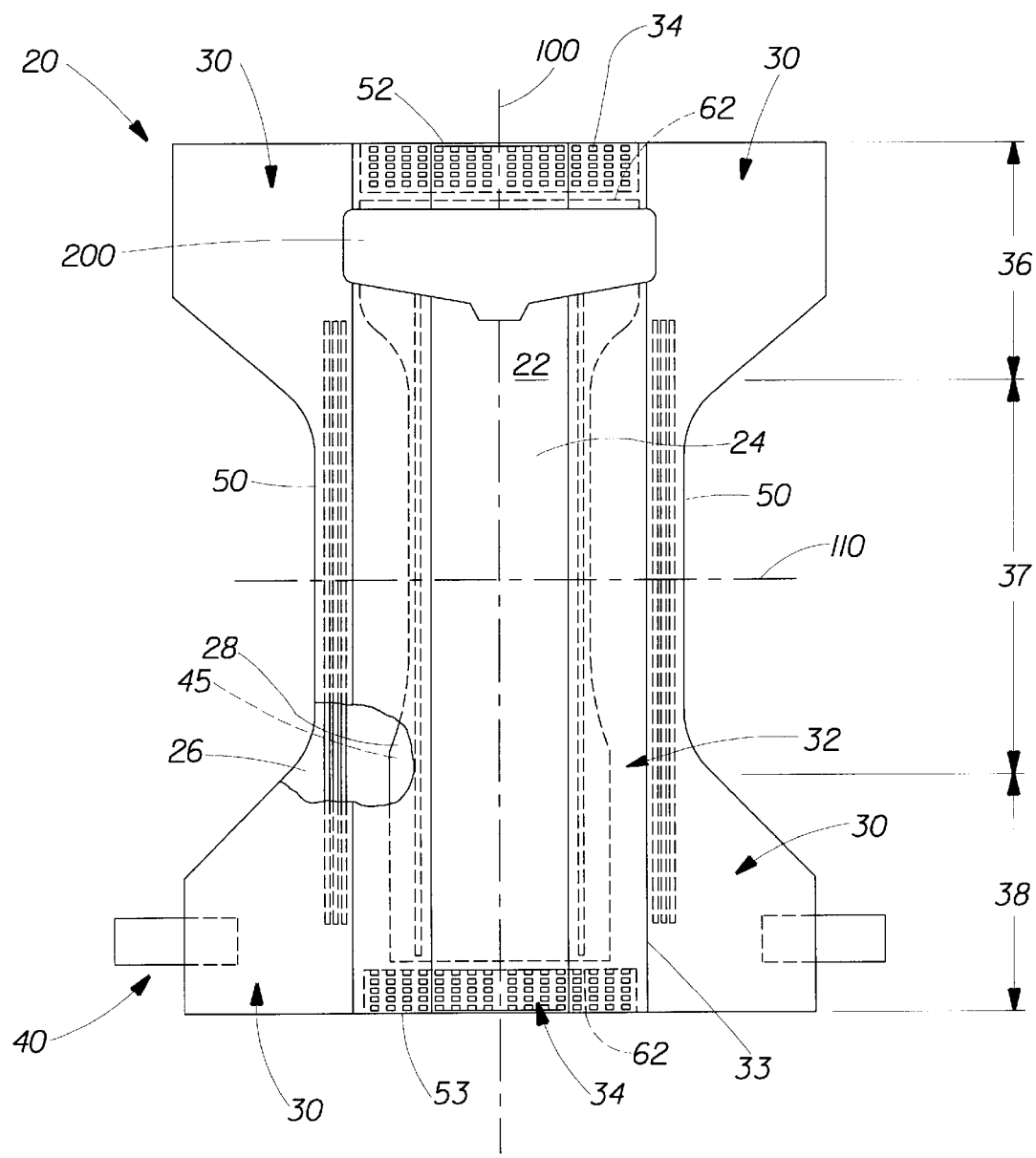
FIG. 1 is a plan view of an absorbent article of the present invention having a portion cut away to reveal the underlying structure, the body-facing surface of the article facing the viewer.

As used herein, the term "absorbent article" refers to devices which absorb and contain body exudates and, more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as absorbent articles (i.e., they are intended to be discarded after a single use and, preferably, to be recycled, composted or otherwise discarded in an environmentally compatible manner). A "unitary" absorbent article refers to absorbent articles which are formed of separate parts united together to form a coordinated entity so that they do not require separate manipulative parts like a separate holder and/or liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, bandages and the like.

As used herein, the "longitudinal" dimension, direction, or axis of the diaper is aligned front to back with respect to the wearer as the disposable absorbent article is worn. The "lateral" or "transverse" dimension, direction, or axis of the diaper is orthogonal to the longitudinal direction and is sideways aligned as the diaper is worn. The "Z-direction" is orthogonal to both the longitudinal and transverse directions.

As used herein "climate" pertains to the temperature and relative humidity of a space.

This invention is an improved absorbent article, such as a disposable diaper, which assists in drying the skin of a wearer which is often damp due to perspiration and exposure to an environment having a high relative humidity as a result of evaporation of urinary waste. The invention provides a method for moving fresh air through the absorbent article as the article is worn. Moving air increases the coefficient of convective heat transfer from the skin, moving from the realm of free convection, where it is with current absorbent products, to forced convection. This forced convection can increase the heat transfer and thus, cool the skin of the wearer while lowering the relative humidity inside of the product (as, in general, the outside relative humidity is lower than the relative humidity inside of the absorbent article), the combination of which generally results in dryer skin and improved comfort for the wearer.

In its simplest embodiment, the disposable diaper of this invention (hereinafter referred to simply as the "diaper"), comprises a liquid permeable topsheet which, in use, is placed next to the user's body; a backsheet which, in use, is placed remote from the user's body and adjacent to any outer garment the user should happen to be wearing; a main absorbent core and a bellows 200. The bellows 200 utilizes biomechanical motion of the wearer to collapse and expand the same in order to force the circulation of air throughout the diaper. "Biomechanical motion" refers to movement associated with the mechanical bases of muscular activity such as abdominal expansion and contraction caused by breathing or movement of the lower torso region during walking and crawling. The bellows 200 is designed with one-way flaps, such that air can be predominantly forced out through outlet ports when the bellows 200 is compressed, and can be predominantly drawn in through inlet ports when the bellows 200 expands.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28 which is preferably positioned between at least a portion of the topsheet 24 and the backsheet 26; side panels 30; elasticized leg cuffs 32; an elastic waist feature 34; and a fastening system generally designated 40. The diaper 20 is shown in FIG. 1 to have a first waist region, such as a front waist region 36, a second waist region, such as a rear waist region 38 opposed to the front waist region 36, and an intermediate region, such as a crotch region 37, located between the front waist region 36 and the rear waist region 38. The front waist region 36 and the rear waist region 38 are those portions of the diaper 20 which, when worn, encircle the waist of the wearer and are generally the highest elevation of the diaper 20 when the wearer is in the standing position. The crotch region 37 is disposed between the front and rear waist regions and is the part of the diaper which, when worn, is between the wearer's legs. The periphery of the diaper 20 is defined by the outer edges of the diaper 20 in which longitudinal edges 50 run generally parallel to the longitudinal centerline 100 of the diaper 20 and a first end edge 52 and a second end edge 53 opposite the first end edge 52 run between the longitudinal edges 50 generally parallel to the lateral centerline 110 of the diaper 20. The bellows 200 is generally disposed between the topsheet and the absorbent core and can be affixed to either the topsheet or the core. Although the bellows 200 illustrated in FIG. 1 is positioned in the front waist region, the bellows 200 may be located in any region, preferably the front or rear waist regions where the bellows 200 can most effectively interact with abdominal expansion and contraction associated with the wearer's breathing. Alternatively, the bellows may be disposed in the side panels 30 of the front or rear waist regions 36, 38.

The chassis 22 of the diaper 20 comprises the main body of the diaper 20. The chassis 22 comprises at least a portion of the absorbent core 28 and preferably an outer covering including the topsheet 24 and/or the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease et al. on Dec. 3, 1996; and U.S. Pat. No. 6,004,306 entitled "Absorbent Article With Multi-Directional Extensible Side Panels" issued to Robles et al. on Dec. 21, 1999; each of which is incorporated herein by reference.

The backsheet 26 is generally that portion of the diaper 20 positioned adjacent garment facing surface 45 of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind., USA and sold under the trade names X15306, X10962 and X10964. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Exxon Chemical Co., of Bay City, Tex., USA under the designation EXXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 issued on Aug. 17, 1999 to LaVon et al.; U.S. Pat. No. 5,865,823 issued on Feb. 2, 1999 in the name of Curro; and U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell, et al. on May 21, 1996, and which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. (As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. 3,911,173 issued to Sprague, Jr. on Oct. 7, 1975; U.S. Pat. 4,785,996 issued to Ziecker, et al. on Nov. 22, 1978; and U.S. Pat. 4,842,666 issued to Werenicz on Jun. 27, 1989. Each of these patents is incorporated herein by reference. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent body surface 47 of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to one or more other elements of the diaper 20.

The topsheet 24 is preferably compliant, soft-feeling, and non-irritating to the wearer's skin. Further, at least a portion of the topsheet 24 is liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the topsheet 24 includes fibers, the fibers may be spunbond, carded, wet-laid, meltblown, hydroentangled, or otherwise processed as is known in the art. One suitable topsheet 24 comprising a web of staple-length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries" issued to Thompson on Dec. 30, 1975; U.S. Pat. No. 4,324,246 entitled "Disposable Absorbent Article Having A Stain Resistant Topsheet" issued to Mullane, et al. on Apr. 13, 1982; U.S. Pat. 4,342,314 entitled "Resilient Plastic Web Exhibiting Fiber-Like Properties" issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression" issued to Ahr, et al. on Jul. 31, 1984; and U.S. Pat. No. 5,006,394 "Multilayer Polymeric Film" issued to Baird on Apr. 9, 1991. Other suitable topsheets 26 may be made in accordance with U.S. Pat. Nos. 4,609,518 and 4,629,643 issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, at least a portion of the topsheet 24 is made of a hydrophobic material or is treated to be hydrophobic in order to isolate the wearer's skin from liquids contained in the absorbent core 28. If the topsheet 24 is made of a hydrophobic material, preferably at least a portion of the upper surface of the topsheet 24 is treated to be hydrophilic so that liquids will transfer through the topsheet more rapidly. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and/or immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating a surfactant in the topsheet 24 can be found in U.S. Statutory Invention Registration No. H1670 published on Jul. 1, 1997 in the names of Aziz et al. Each of these references is hereby incorporated by reference herein. Alternatively, the topsheet 24 may include an apertured web or film which is hydrophobic. This may be accomplished by eliminating the hydrophilizing treatment step from the production process and/or applying a hydrophobic treatment to the topsheet 24, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. Nos. 5,607,760 entitled "Disposable Absorbent Article Having A Lotioned Topsheet Containing an Emollient and a Polyol Polyester Immobilizing Agent" issued to Roe on Mar. 4, 1997; U.S. Pat. No. 5,609,587 entitled "Diaper Having A Lotion Topsheet Comprising A Liquid Polyol Polyester Emollient And An Immobilizing Agent" issued to Roe on Mar. 11, 1997; U.S. Pat. No. 5,635,191 entitled "Diaper Having A Lotioned Topsheet Containing A Polysiloxane Emollient" issued to Roe et al. on Jun. 3, 1997; U.S. Pat. No. 5,643,588 entitled "Diaper Having A Lotioned Topsheet" issued to Roe et al. on Jul. 1, 1997; and U.S. Pat. No. 5,968,025 entitled "Absorbent Article Having a Lotioned Topsheet" issued to Roe et al. on Oct. 19, 1999. The lotion may function alone or in combination with another agent as the hydrophobizing treatment described above. The topsheet 24 may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The topsheet 24 may comprise one or more aperture to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the aperture should have an area of between about 10 $cm^2$ and about 50 $cm^2$. The aperture preferably has an area of between about 15 $cm^2$ and 35 $cm^2$.

Further, the topsheet 24 may be fully or partially elasticated or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which is incorporated by reference herein.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735 entitled "High Density Absorbent Members Having Lower Density and Lower Basis Weight Acquisition Zones" issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" issued to Herron et al. on Aug. 11, 1992; U.S. Pat. No. 5,147,345 entitled "High Efficiency Absorbent Articles For Incontinence Management" issued to Young et al. on Sept. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From High Internal Phase Emulsions Having Very High Water-To-Oil Ratios" issued to DesMarais et al. on Jul. 22, 1997. Each of these patents is incorporated herein by reference.

The diaper 20 may also include a sublayer disposed between the topsheet 24 and the backsheet 26. (As used herein, the term "disposed" is used to mean that an element (s) of the diaper is formed (joined and positioned) in a particular place or position as a unitary structure with other elements of the diaper or as a separate element joined to another element of the diaper.) The sublayer may be any material or structure capable of accepting, storing or immobilizing bodily exudates. Thus, the sublayer may include a single material or a number of materials operatively associated with each other. Further, the sublayer may be integral with another element of the diaper 20 or may be one or more separate elements joined directly or indirectly with one or more elements of the diaper 20. Further, the sublayer may include a structure that is separate from the core 28 or may include or be part of at least a portion of the core 28.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in European Patent Application No. EP 0 847 738 A1 entitled "Disposable Absorbent Article Having Capacity to Store Low-Viscosity Fecal Material" published Jun. 17, 1998 in the name of Roe and U.S. Pat. No. 5,941,864 entitled "Disposable Absorbent Article Having Improved Fecal Storage" issued to Roe on Aug. 24, 1999, both of which are hereby incorporated by reference herein. Further, the sublayer, or any portion thereof, may include or be coated with a lotion or other known substances to add, enhance or change the performance or other characteristics of the element.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 62 of the absorbent core 28 and generally forms at least a portion of the first and second end edges 52 and 53 of the diaper 20. Disposable diapers are often constructed so as to have two elastic waist features, one positioned in the front waist region 36 and one positioned in the rear waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also include a fastening system 40. The fastening system 40 preferably maintains the front waist region 36 and the rear waist region 38 in an overlapping configuration so as to provide lateral tensions about the circumference of the diaper 20 to hold the diaper 20 on the wearer. The fastening system 40 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; the herein before referenced U.S. Pat. No. 5,151,092 issued to Buell on Sep. 9, 1992; and U.S. Pat. No. 5,221,274 issued to Buell on Jun. 22, 1993. The fastening system 40 may also provide a means for holding the article in a disposal configuration as disclosed in U.S. Pat. No. 4,963, 140 issued to Robertson et al. on Oct. 16, 1990. Each of these patents is incorporated herein by reference. In alternative embodiments, opposing sides of the article may be seamed or welded to form a past. This allows the article to be used as a pull-on type diaper, such as a training pant.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaper pulls one elasticized side panel 30 farther than the other during application, the diaper 20 will "self-adjust" during wear.

While the diaper 20 of the present invention preferably has the side panels 30 disposed in the rear waist region 38, the diaper 20 may be provided with side panels 30 disposed in the front waist region 36 or in both the front waist region 36 and the rear waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; and U.S. Pat. No. 6,004,306 entitled "Absorbent Article With Multi-Directional Extensible Side Panels" issued to Robles et al. on Dec. 21, 1999; each of which is incorporated herein by reference.

The diaper 20 preferably further includes leg cuffs 32 which provide improved containment of liquids and other body exudates. Leg cuffs 32 may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs 32 with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper 20, and the like, or any combinations thereof Examples of pockets and spacers for use in absorbent products are described in U.S. Pat. 5,514,121 issued to Roe et al. on May 7, 1996, entitled "Diaper Having Expulsive Spacer"; U.S. Pat. No. 5,171,236 issued to Dreier et al. on Dec. 15, 1992 entitled "Disposable Absorbent Article Having Core Spacers"; U.S. Pat. No. 5,397,318 issued to Dreier on Mar. 14, 1995 entitled "Absorbent Article Having A Pocket Cuff"; U.S. Pat. 5,540, 671 issued to Dreier on Jul. 30, 1996 entitled "Absorbent Article Having A Pocket Cuff With An Apex"; PCT Application WO 93/25172 published Dec. 3, 1993 entitled "Spacers For Use In Hygienic Absorbent Articles And Disposable Absorbent Articles Having Such Spacer"; U.S. Pat. No. 5,306,266 entitled "Flexible Spacers For Use In Disposable Absorbent Articles" issued to Freeland on Apr. 26, 1994; and U.S. Pat. No. 5,997,520 entitled "Disposable Absorbent Article With Selectively Expandable or Inflatable Component" issued to Ahr et al. on Dec. 7, 1999. Examples of compartments or voids are disclosed in U.S. Pat. No. 4,968, 312 entitled "Disposable Fecal Compartmenting Diaper" issued to Khan on Nov. 6, 1990; U.S. Pat. No. 4,990,147 entitled "Absorbent Article With Elastic Liner For Waste Material Isolation" issued to Freeland on Feb. 5, 1991; U.S. Pat. No. 5,62,840, entitled "Disposable Diapers" issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets" issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition issued Aug. 5, 1997 to Roe, et al. Examples of other structures especially suitable for management of low viscosity feces are disclosed in U.S. Pat. No. 5,941,864 issued to Roe et al. on Aug. 24, 1999; U.S. Pat. No. 5,977,430 issued to Roe et al. on Nov. 2, 1999 and U.S. Pat. No. 6,013,063 issued to Roe et al. on Jan. 11, 2000. All of the above-cited references are hereby incorporated by reference herein.

Figure 2:
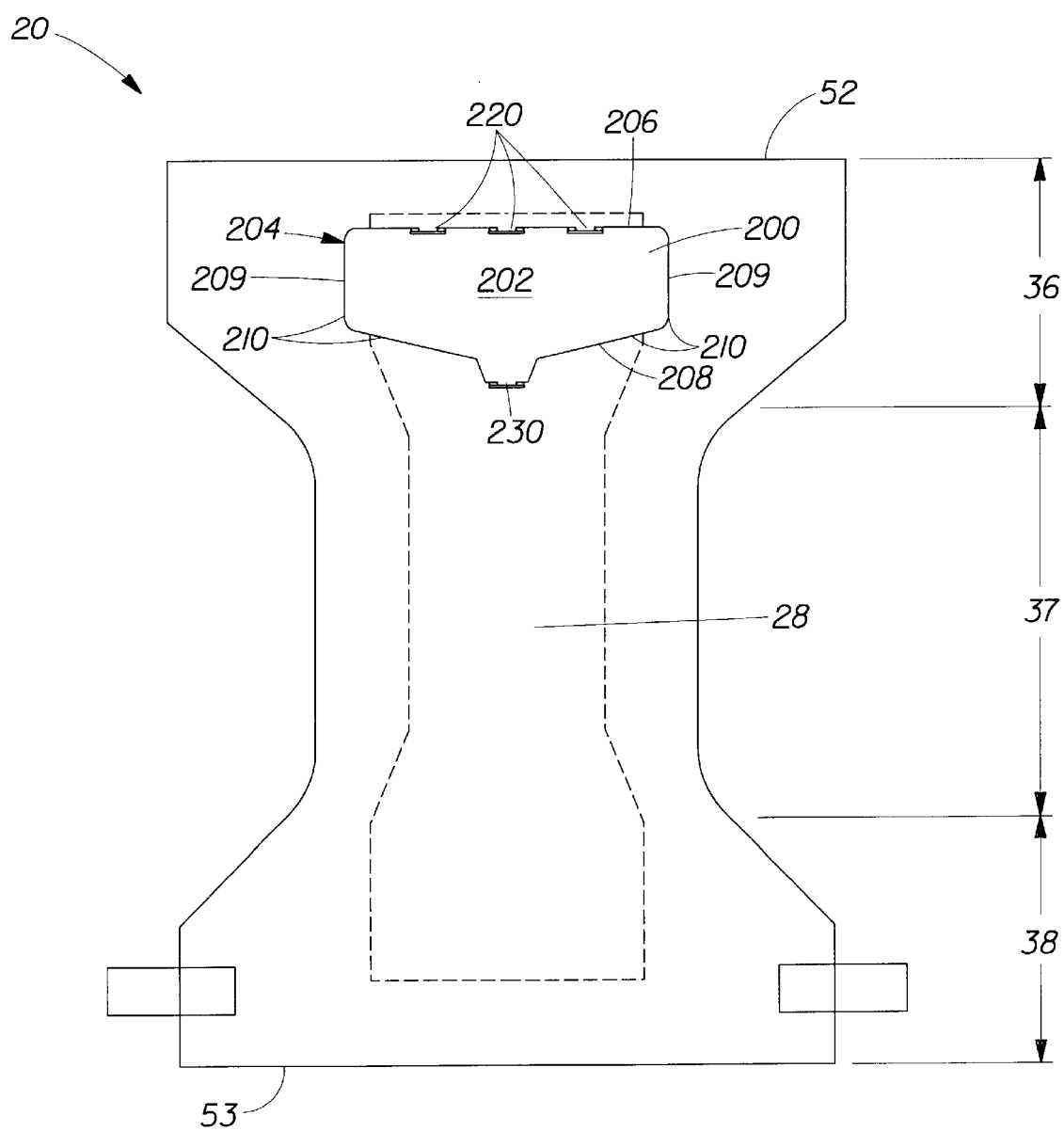
FIG. 2 is a plan view of an absorbent article embodiment of the present invention depicting elements of the bellows.

The diaper of the present invention may include a bellows which is repeatably deformable to force airflow through the diaper in a controlled manner. Such airflow can assist in drying the skin of the wearer as well provide a cooling effect to the skin. As shown in FIG. 2, the bellows 200 comprises a chamber having a volume of air enclosed by chamber walls 210 with one or more inlet ports 220 and one or more outlet ports 230. When subjected to a compression load, the chamber walls 210 contract expelling the volume of air through the outlet ports 230. Once the compressive load is released, the chamber walls 210 expand drawing a fresh volume of air into the chamber through the inlet ports 220. This operation can be sustained by providing resilient chamber walls 210 that are gas impermeable and inlet 220 and outlet ports 230 permitting flow in one direction and minimizing return flow. By "resilient chamber walls" it is meant that the chamber walls 210 can be repeatedly deformed by a force causing air to be forced out of the chamber through the outlet ports 230 and that upon release of the force the chamber walls 210 generally resume their undeformed shape, thereby causing air to be drawn into the chamber through the inlet ports 220. The resilient chamber walls 210 can be formed from a material such as rubber, thermoplastic polymer, or any other suitable material or combination of material. Suitable resilient walls can be molded from an Estane 5708 F1 Polyester-Urethane polymer to have a thickness of about 0.3 millimeters.

The chamber walls 210 comprise a first, body facing side 202, a second side 204 opposite the body facing side 202, a first end, such as an upper end 206, and a second end, such as a lower end 208. The upper end 206 faces the point of highest elevation on the diaper 20 (such as first end edge 52 or second end edge 53) while the lower end 208 faces the point of lowest elevation on the diaper 20 (such as the crotch region 37). The diaper 20 illustrated in FIG. 2 shows the upper end 206 of the bellows 200 oriented adjacent to the first end edge 52 of the diaper 20 and the lower end 208 of the bellows 200 oriented towards the crotch region 37 of the diaper 20. In this arrangement, inlet ports 220 are disposed in the upper end 206 to draw fresh air into the chamber and an outlet port 230 is disposed in the lower end 208 to expel the fresh air out of the chamber into the crotch region 37. In order to increase the velocity of the airflow exiting the bellows 200, the walls 210 forming the lower end 208 can be tapered toward the outlet port 230 forming a funnel or nozzle, thereby decreasing the outlet port area and thus, increasing the air velocity for the same volume of air.

The bellows 200 can be disposed between the topsheet 24 and the absorbent core 28 in which case the second side 204 of the chamber can be attached to the absorbent core 28 by adhesive bonding. Alternatively, the body facing side 202 of the chamber can be attached to the topsheet 24 by heat/pressure sealing, adhesive bonding, or ultrasonic bonding. Further, the bellows 200 may be disposed between the backsheet 26 and the absorbent core 28 or between the topsheet 24 and the backsheet 26.

The orientation of the bellows 200 and the disposition of the inlet and outlet ports 220, 230 are not limited to the embodiment depicted in FIG. 2. For instance, the orientation of the bellows 200 can be reversed so that the lower end 208 is adjacent to the first end edge 52 of the diaper 20 and the upper end 206 is oriented towards the crotch region 37 of the diaper 20. For this arrangement, expansion of the bellows 200 draws humid air into the chamber from the crotch region 37 while contraction expels the humid air through the outlet port 230 near the first end edge 52 of the diaper 20. Further, the location of the inlet ports 220 need not be limited to the upper 206 or lower 208 ends of the bellows 200. For instance, single or multiple inlet ports 220 can be disposed in the opposing side ends 209 of the bellows 200. In addition, the outlet port 230 can comprise a body facing aperture which directs the exiting airflow towards the skin of the wearer.

Figure 3A:
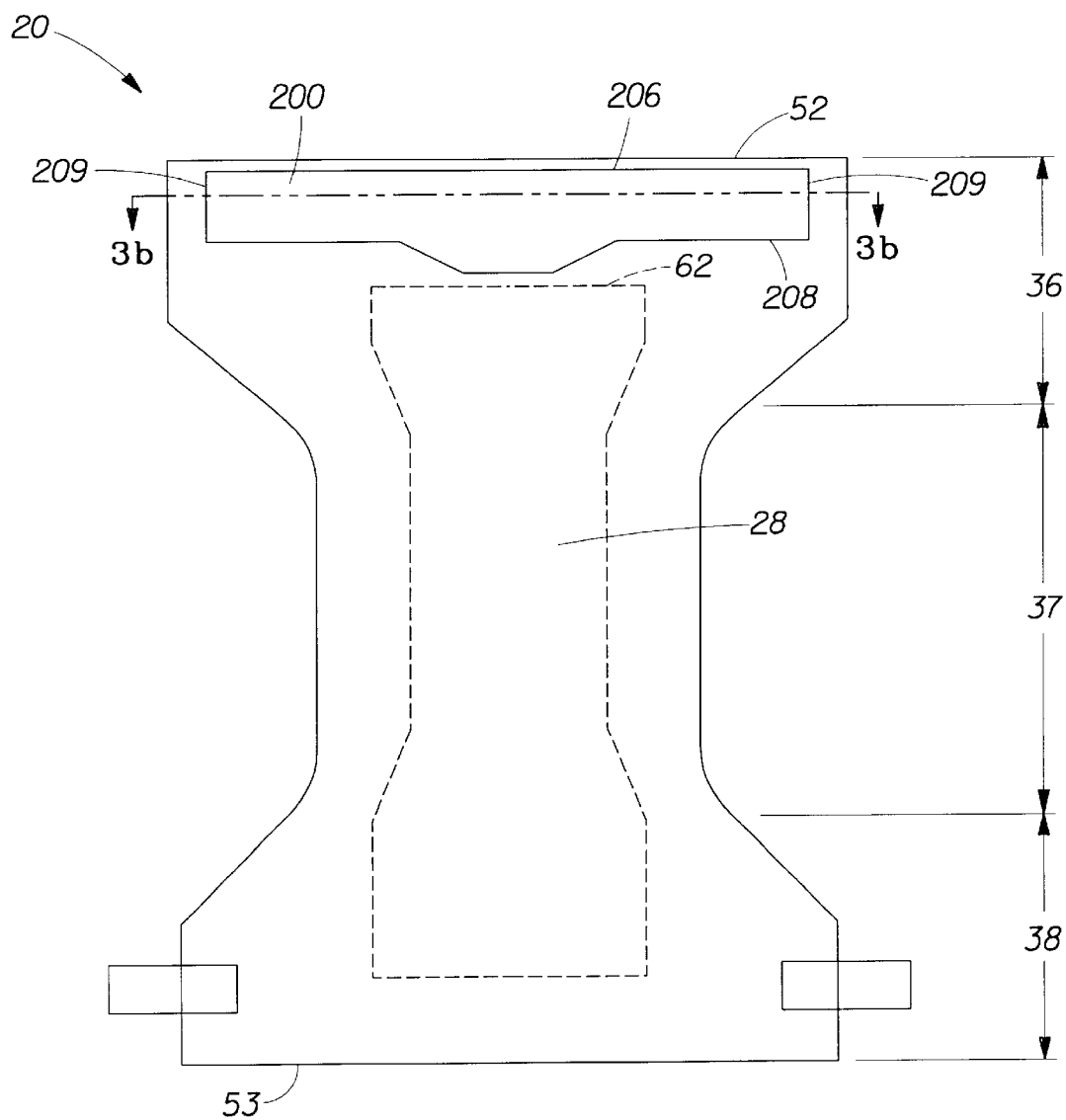
FIG. 3a is a plan view of an embodiment of the present invention showing the bellows disposed in a space between the first edge end of the absorbent article and a waist edge of the absorbent core.
Figure 3B:
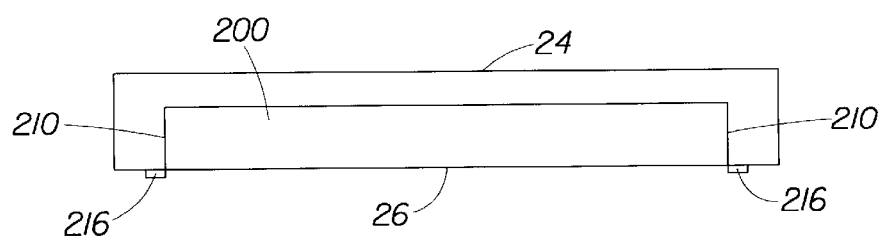
FIG. 3b is a cross sectional view of the absorbent article illustrated in FIG. 3a showing the attachment of the bellows to the backsheet.

In an alternate embodiment illustrated in FIG. 3a, the bellows 200 can be disposed outboard of a waist edge 62 of the absorbent core 28 between the topsheet 24 and the backsheet 26 towards the first end edge 52 of the diaper 20. For this configuration, as shown in FIG. 3b, the chamber walls 210 can be joined directly to the backsheet 26 along seams 216, with the backsheet 26 forming a portion of the chamber by furnishing a chamber wall. Such may be desirable in order to minimize the thickness of the diaper 20. The seams 216 can be formed by any suitable method, including but not limited to heat/pressure sealing, adhesive bonding, or ultrasonic bonding.

Figure 4A:
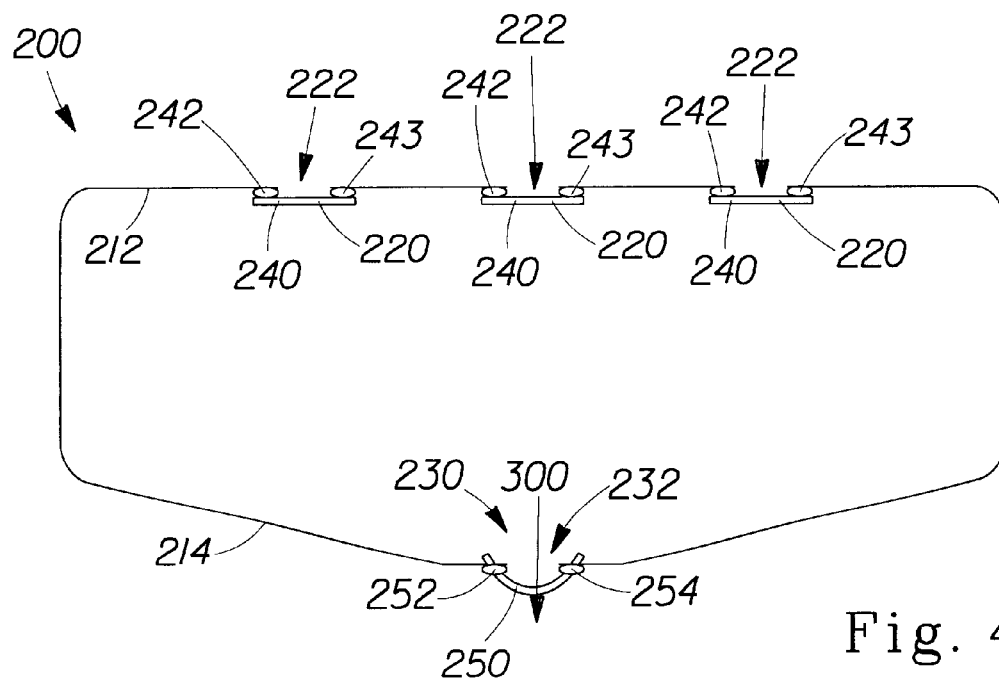
FIG. 4a is a plan view of the bellows portrayed in the aforementioned figures showing airflow exiting the bellows through a one-way flap of an outlet port.
Figure 4B:
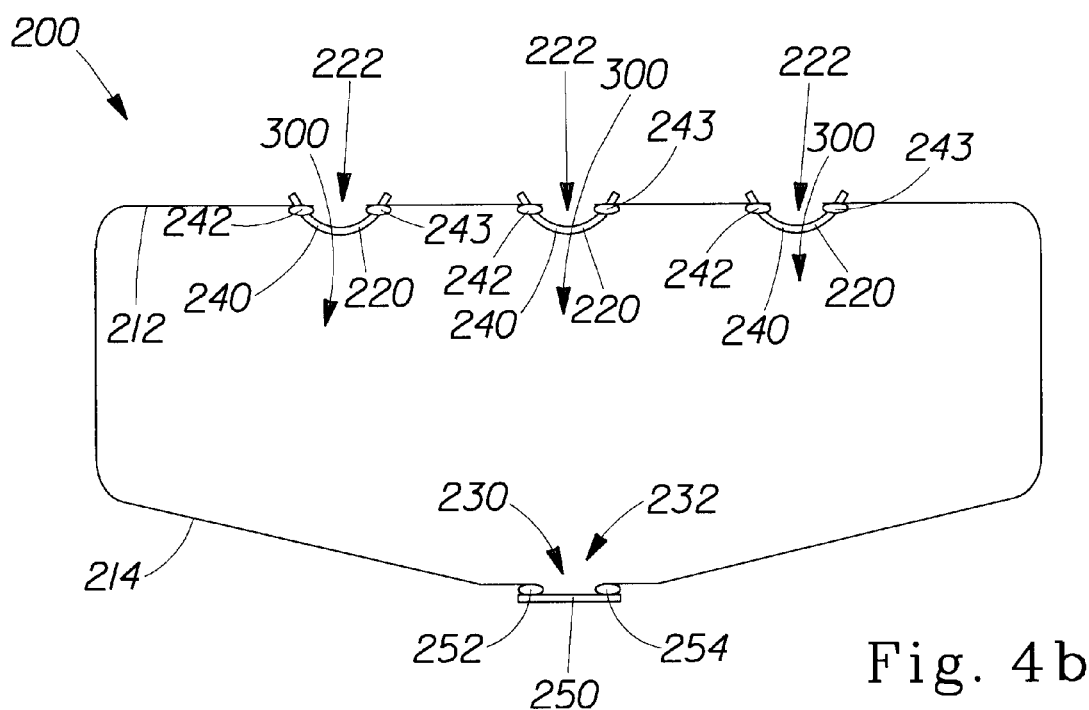
FIG. 4b is a plan view of the bellows portrayed in the aforementioned figures showing the airflow entering the bellows through one-way flaps of inlet ports.

FIGS. 4a and 4b, depict exemplary embodiment inlet port one-way flaps 240 joined to the internal surface 212 the chamber wall 210 providing unidirectional airflow 300 entering the chamber through the inlet port 220. The one-way flaps 240 are deformable and supported at first and second ends 242, 243 which are attached to the internal surface 212 of the chamber. When the air pressure in the chamber is greater than the pressure outside of the chamber (e.g. when the chamber is contracting), the pressure differential causes the flaps 240 to cover the apertures 222 of the inlet ports 220, as depicted in FIG. 4a, thereby preventing the airflow 300 from exiting the chamber through the inlet ports 220. When the air pressure in the chamber is less than the pressure outside the chamber (e.g. when the chamber is expanding), the pressure differential deforms the flaps 240 intermediate the first and second ends 242, 243, as shown in FIG. 4b, permitting the airflow 300 to enter the chamber through the inlet port apertures 222.

The same type of one-way flap can be used at the outlet port 230 assembled in reverse order from the inlet port one-way flaps 240 described above. At the outlet port 230 depicted in FIG. 4a, a one-way flap 250 is supported at first and second ends 252, 254 attached to the external surface 214 of the chamber. When the air pressure in the chamber is greater than the pressure outside of the chamber (e.g. when the chamber is contracting), the pressure differential deforms the flap 250 intermediate the first and second ends 252, 254, as shown in FIG. 4a, permitting airflow 300 to exit the chamber through the outlet port aperture 232. When the air pressure in the chamber is less than the pressure outside the chamber (e.g. when the chamber is expanding) the pressure differential causes the flap 250 to cover the outlet port aperture 232, as depicted in FIG. 4b, thereby preventing airflow 300 from entering the chamber through the outlet port aperture 232.

Figure 5A:
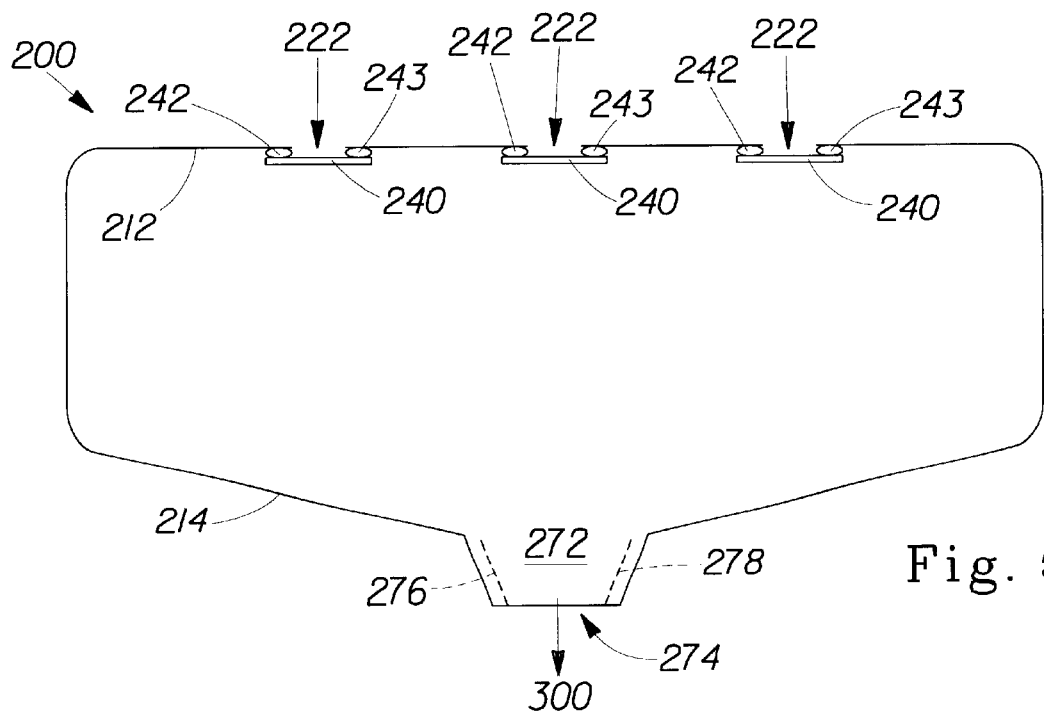
FIG. 5a is a plan view of an alternate embodiment of the bellows illustrated in FIGS. 4a and 4b wherein the one-way flap at the outlet port is replaced by two flexible flaps providing unidirectional flow exiting the bellows.
Figure 5B:
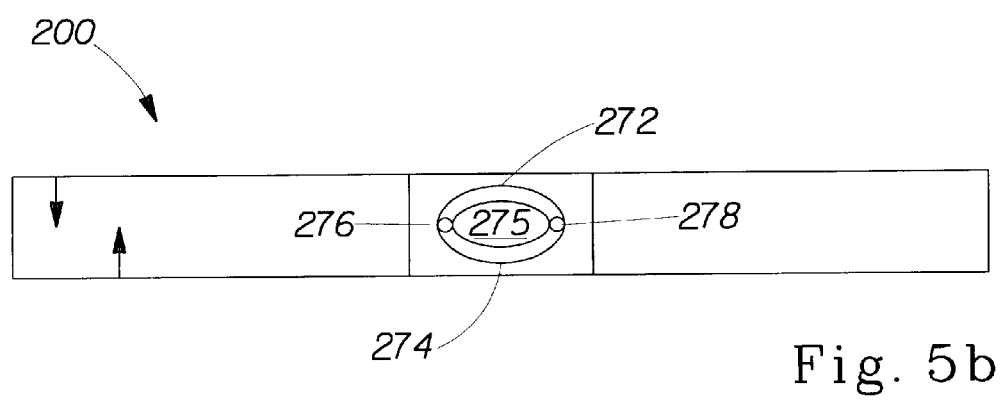
FIG. 5b is a cross sectional view of the bellows illustrated in FIG. 5a depicting the flexible flaps in the open configuration allowing airflow to exit the outlet port.
Figure 5C:
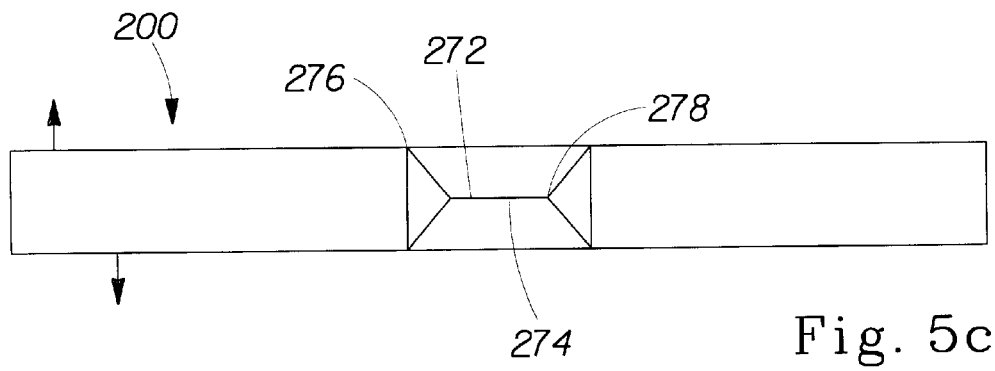
FIG. 5c is a cross sectional view of the bellows illustrated in FIG. 5a depicting the flexible flaps in the closed configuration.

In an alternate embodiment shown in FIG. 5a, the outlet port 230 comprises two flexible flaps 272, 274 attached to the outlet port 230 and joined along opposing edges 276, 278 and forming a flowpath 275 therebetween. When the air pressure in the chamber is greater than the pressure outside of the chamber (e.g. when the chamber is contracting), the pressure differential deforms the flexible flaps 272, 274 intermediate the opposing connected edges 276, 278 forming the flowpath 275 as depicted in FIG. 5b. This enables the airflow 300 to exit the chamber through the outlet port aperture 232. When the air pressure in the chamber is less than the pressure outside the chamber (e.g. when the chamber is expanding) the pressure differential causes the flexible flaps 272, 274 to collapse and seal off the flowpath 275, as depicted in FIG. 5c, preventing airflow 300 from entering the chamber through the outlet port aperture 232.

Figure 6A:
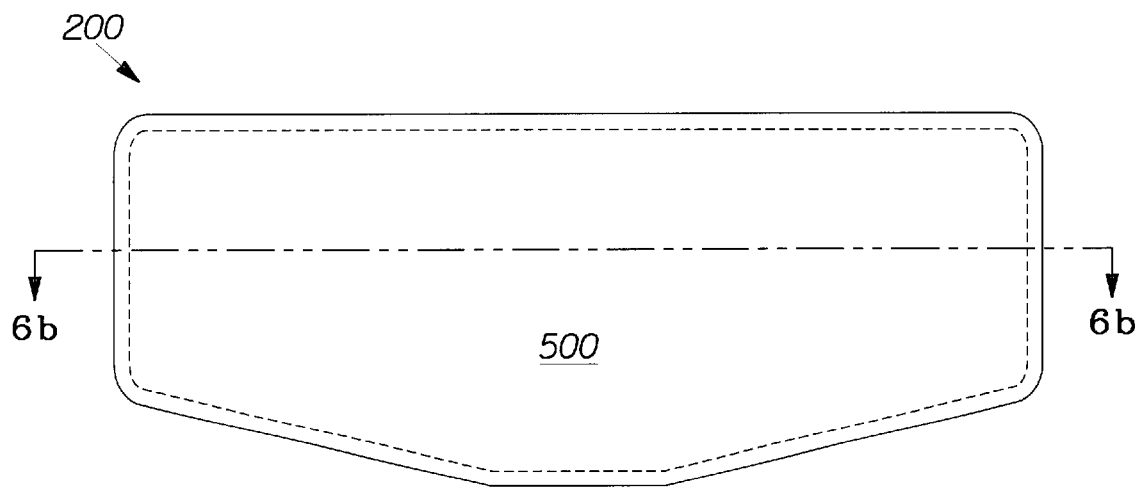
FIG. 6a is a plan view an embodiment of the present invention showing a resilient insert disposed within the bellows chamber.
Figure 6B:
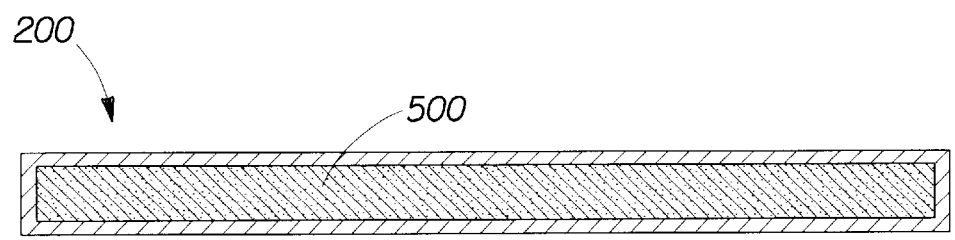

In an alternate embodiment shown in FIGS. 6a and 6b, the bellows 200 includes a resilient element 500 disposed within the bellows chamber. By "resilient element" it is meant an element that can be compressed by a compressive loading from a first thickness to a second thickness less than or equal to about 60 percent of the first thickness, and that element regains at least about 70 percent of its first thickness within about 15 seconds of release of the compressive loading. The resilient element can be compressed, such as by abdominal expansion of the wearer while inhaling, to force air from the chamber through the outlet port. Upon release of the force compressing the resilient element, such as abdominal contraction of the wearer while exhaling, the resilient element expands, thereby drawing a fresh supply of air into the bellows chamber through the inlet port.

The resilient element 500 preferably has a relatively low resistance to compressive loading allowing the resilient element 500 to be easily compressed. The resilient element 500 preferably can be compressed from a first thickness to a second thickness less than or equal to about 60 percent of the first thickness by a compressive loading of no more than about 0.33 pound per square inch.

Figure 8A:
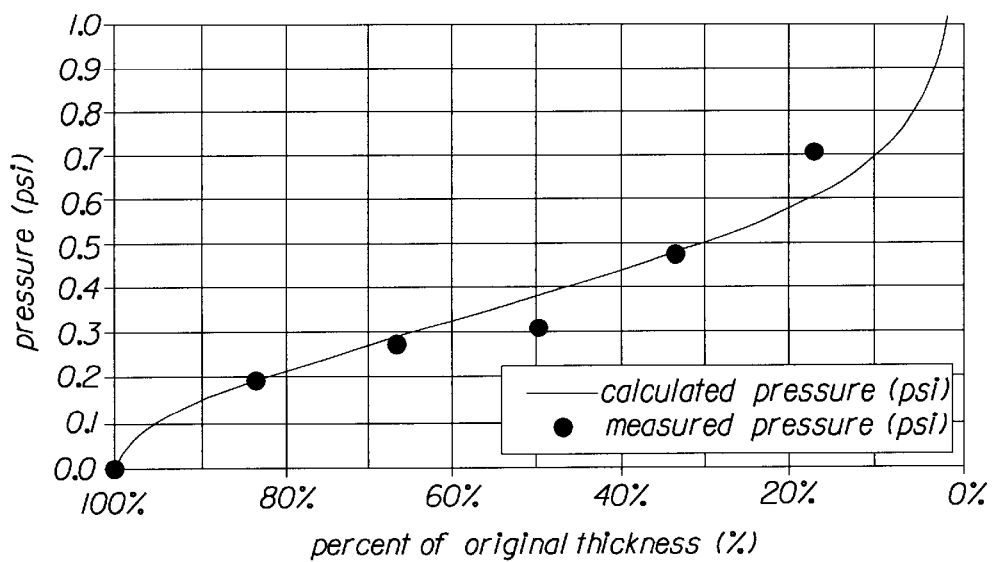
FIG. 8a is a chart providing a calculated pressure curve for a resilient element depicted in FIGS. 6a and 6b fit from data measured on a compression tester.

For example, a resilient element 500 of the present invention comprising a 2.0 inch×2.25 inch piece of foam having original thickness of approximately 0.94 inches (24 mm) was tested under various compressive loadings as illustrated by the chart in FIG. 8a. The chart provides a calculated pressure curve fit from data measured on a compression tester (referenced below). For instance, under a load of approximately 0.33 psi the piece of foam compressed to 60% of its original thickness (0.57 inches). At an applied load of about 0.5 psi, the foam compressed to approximately 30% of the original thickness. Finally, at an applied load of 1 psi the piece of foam compressed to about 10% of the original thickness, approaching the foams compressive limit.

During the compression testing, the load applicator fully covered the 2.0 inch×2.25 inch piece of foam. A suitable compression testing device for compressing a resilient element 500 is a CHATILLON DIGITAL FORCE GAUGE DFIS 10.

The resilient element 500 should be capable of being cyclically compressed without substantial loss of its unloaded caliper between compression cycles, so that the bellows 200 can be successively activated by repeatably compressing and releasing the resilient element 500. Preferably, the resilient element 500 may be capable of being cyclically compressed at least 25 times per minute to less than about 60% of its initial, unloaded caliper on each compression cycle, with the resilient element 500 regaining at least about 75% of its initial caliper intermediate each compression cycle. More preferably, the resilient element 500 may be capable of being cyclically compressed at least 10 to 20 times per minute to less than about 60% of its initial, unloaded caliper on each compression cycle, with the resilient element 500 regaining at least about 75% of its initial caliper intermediate each compression cycle.

In one embodiment the resilient element 500 can be porous so that air drawn into the bellows chamber 305 is drawn into the resilient element 500, as well as into the space in the chamber 305 not occupied by the resilient element 500. A suitable resilient element 500 can be formed from a sponge or foam material. In one embodiment, the resilient element 500 can comprise an open celled foam. By "open celled" it meant that the individual cells of the foam are for the most part not completely isolated from each other by the material of the cell walls. The resilient element 500 can have a density of between about 0.01 gram per cubic centimeter and about 0.1 gram per cubic centimeter (gm/cc), as measured under a confining pressure of about 0.0125 pound per square inch applied with a load application foot having a diameter of about 1.5 inch.

One suitable open celled foam from which the resilient element 500 can be made is polyurethane foam having a density of between about 0.015 and about 0.025 gm/cc, such is available as #1230 foam from the American Excelsior Corp. of Cincinnati, Ohio. Other suitable materials from which the resilient element 500 can be made include natural sponge materials having a density of between about 0.015 gm/cc and about 0.025 gm/cc, and polyethylene foam having a density of between about 0.020 gm/cc and about 0.030 gm/cc. Another suitable open celled foam is a foam prepared by polymerizing a high internal phase emulsion, such as is described in U.S. Pat. No. 5,147,345 issued Sep. 15, 1992 to Young et al., which patent is incorporated herein by reference.

Figure 7A:
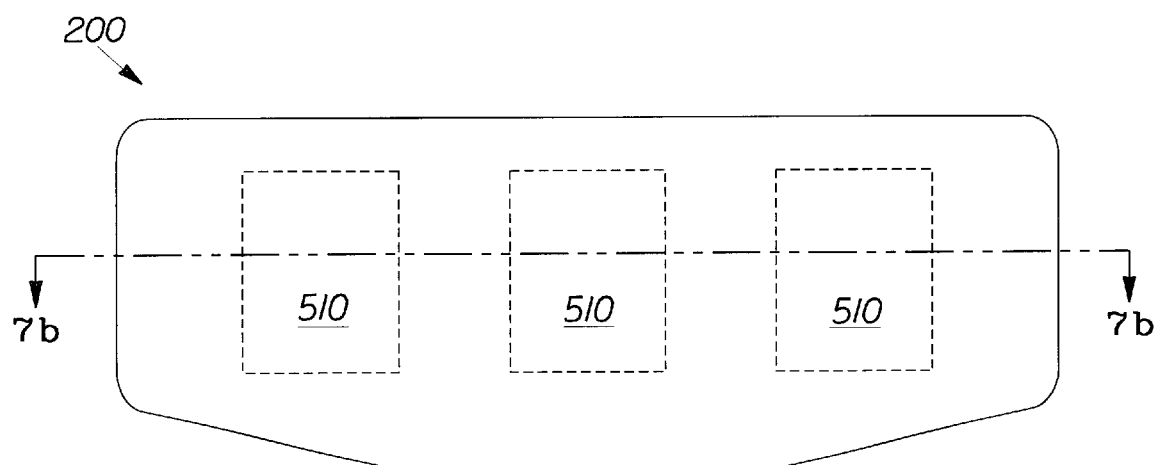
FIG. 7a is a plan view of an alternate embodiment of the bellows depicted in FIG. 6a wherein the resilient insert has been replaced with three resilient elliptically shaped cylinders.
Figure 7B:
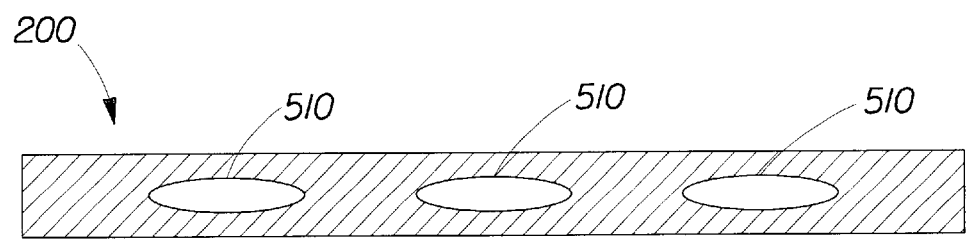

In another embodiment illustrated in FIGS. 7a and 7b, the resilient element 500 comprises one or more deformable, elliptically shaped, hollow cylinders 510 arranged side by side in the bellows chamber. The elliptically shaped cylinders 510 are resilient, enabling them to be repeatably deformed in order to effectively contract and expand the bellows chamber.

The resilient element 500 can have a free, unrestrained Z-direction thickness ranging from about 0.25 inches to about 2.0 inches, more preferably about 0.5 inches to about 1.5 inches and most preferably about 0.7 inches to about 1.25 inches. Prior to use, the resilient element 500 can be compressed to a reduced Z-direction thickness for shipping and storage. For instance, the resilient element 500 can be compressed to a reduced thickness, and the inlet ports 220 can be covered with a releasable seal, such as a piece of adhesive backed film or tape. The seal covering the inlet ports 220 prevents air from air entering the chamber 305, and thereby prevents expansion of the resilient element 500. At the point of use of the disposable absorbent article, the seal covering the inlet ports 220 can be removed, thereby permitting the resilient element 500 to regain its free, unrestrained thickness.

For embodiments utilizing the resilient element 500, the chamber walls 210 are preferably gas impermeable, and can be made from a material which is soft and flexible. In one embodiment, the walls 210 of the chamber can be formed from an elastomeric or stretchable film. Suitable materials include, but are not limited to, thermoplastic films, natural rubbers and laminated films of natural rubber and synthetic thermoplastics. Suitable thermoplastic films include a polyethylene film available from Tredgar Industries designated C-8323 and materials from which the backsheet can be formed, such as Tredgar X8297 and the Clopay P-18-1401 films listed above.

The volume of fresh air expelled from the bellows over a period of time, and the velocity at which that air will flow over the surface of the wearer's skin are relevant factors for effective operation of the bellows. This is determined by such variables as the volume displacement of the bellows chamber, and the period of time required for compression and expansion of the chamber. The time period for compression and expansion is dictated by the biomechanical motion of the wearer which can include breathing, bending and leg motion. The volume of fresh air introduced into the diaper for a given compression cycle is determined by the area in contact with the wearer along with the amount of compression undergone by the bellows chamber. The area in contact with the wearer is the body facing region of the bellows previously described. The minimum area in contact with the wearer can range from about 3.0 square inches. The maximum area in contact with the wearer is dependent on the size of the wearer. For instance, a bellows for an infant weighing between 20 and 30 pounds may have a contact area of about 11 square inches.

The velocity of the airflow exiting the bellows can be determined by the volume displacement rate and the outlet port area(s). The volume displacement rate is generally dependent upon the size of the bellows. For example, a bellows having a contact area of about 11 square inches ($in^2$) which is compressed to about 60% of the original thickness over the full contact area, approximately 12 times per minute may have a volume displacement rate of approximately 0.8 $in^3$/sec (48 $in^3$/minute).

For the present invention, (assuming an average of at least 1 compression to 60% of the original thickness per minute) the bellows can be made to deliver a minimum volume displacement rate of preferably about 1 $in^3$/minute and more preferably at least 4 $in^3$/minute. Likewise, (assuming an average of at least 10 compressions to 60% of the original thickness per minute) the bellows can preferably deliver a maximum volume displacement rate of at least 40 $in^3$/minute and more preferably at least 50 $in^3$/minute.

The velocity of the airflow exiting the bellows can be determined given the volume displacement rates and the flow area of the outlet ports. Since the airflow exits the bellows while the bellows is under compression, the velocity measured van be determined based on the time that the bellows undergoes compression during every minute of a wear time which is dictated by the biomechanical motion of the wearer. For the present invention, the bellows may undergo compression at least 2 seconds of every minute of wear time, more preferably at least 10 seconds of every minute of wear time and most preferably at least 20 seconds of every minute of wear time.

Figure 8B:
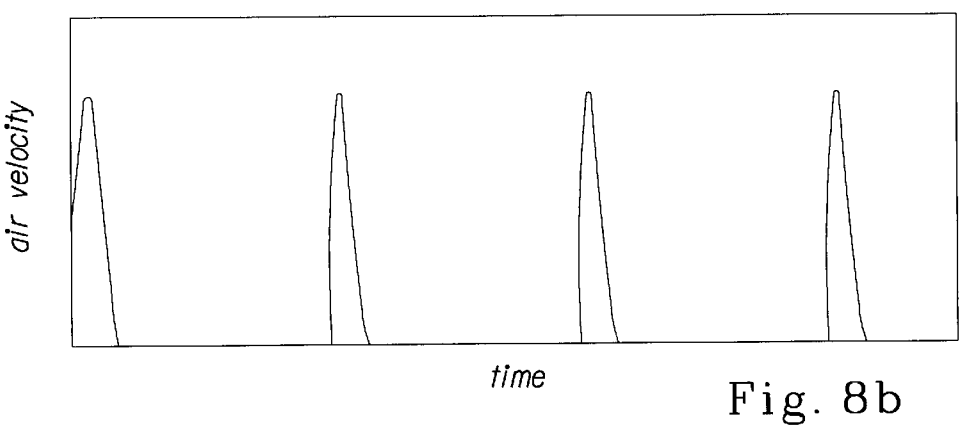
FIG. 8b is a plot of airflow velocity versus time for the airflow produced by the bellows of the present invention.

For the present invention, the bellows preferably can deliver fresh air at a velocity of at least 1 in/sec during an average of at least 2 seconds of every minute of wear time for an average volume rate of 1 in$^3$/minute. The bellows more preferably can deliver fresh air at a velocity of at least 5 in/sec during an average of at least 2 seconds of every minute of wear time for an average volume rate of at least 4 in$^3$/minute. The bellows most preferably can deliver fresh air at a velocity of at least 5 in/sec during an average of at least 20 sec of every minute of wear time for an average volume rate of at least 40 in$^3$/minute. A velocity vs. time plot for the bellows is depicted in the graph on FIG. 8b.

Figure 9A:
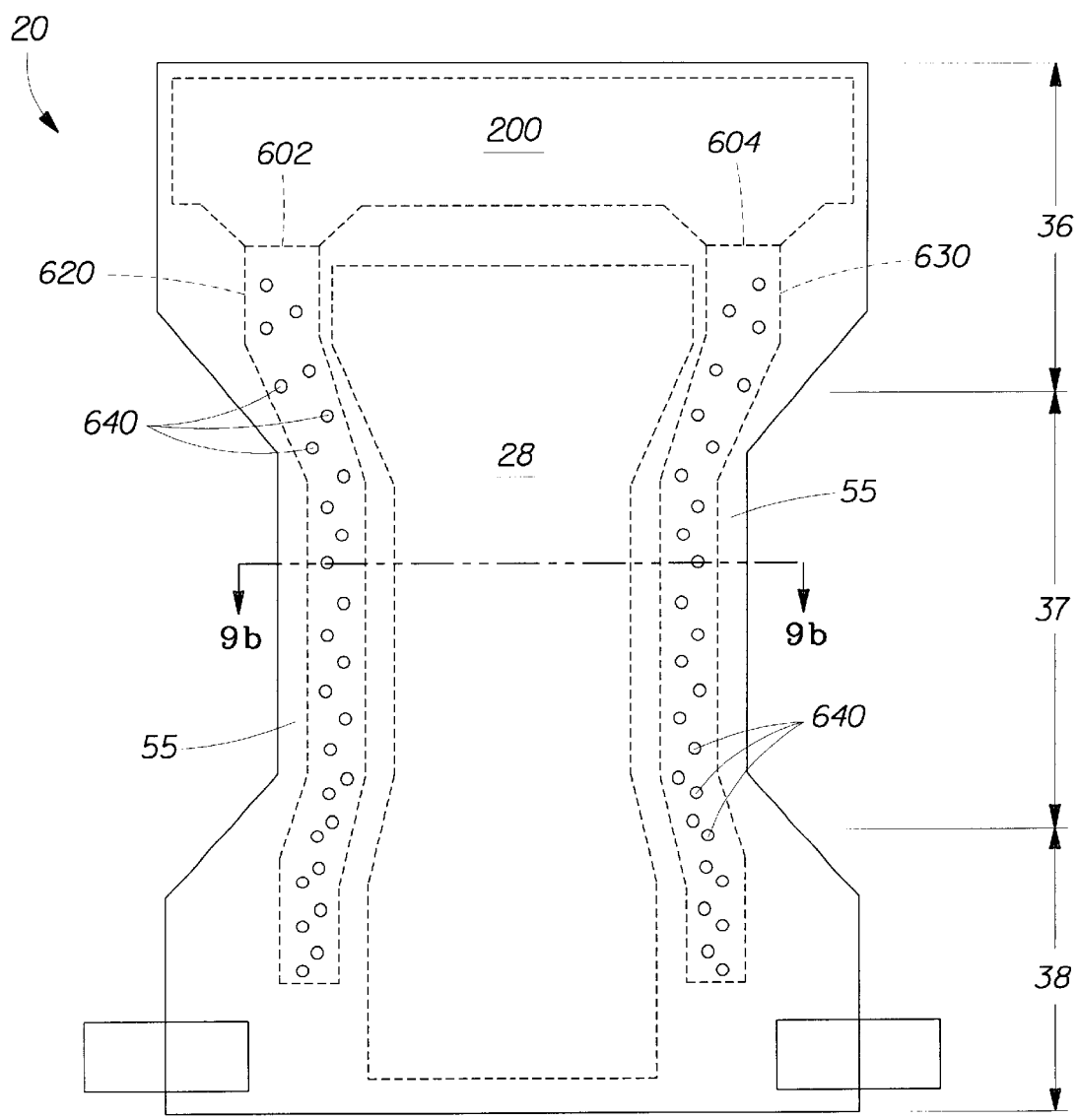
FIG. 9a is a plan view of a disposable absorbent article embodiment of the present invention which includes two air accumulators disposed at two outlet ports of the bellows.
Figure 9B:
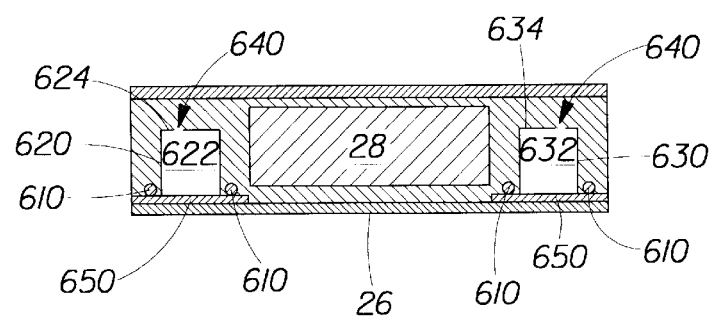
FIG. 9b is a cross sectional view of the absorbent article depicted in FIG. 8a showing the assembly of the air accumulators.

In one embodiment shown in FIGS. 9a and 9b, the bellows 200 includes two outlet ports 602, 604 and comprises inflatable air accumulators 620, 630 attached to the outlet ports 602, 604. The air accumulators 620, 630 have body facing sides with a plurality of apertures 640 disposed therein. The plurality of apertures 640 are arranged along the length of the air accumulators 620, 630 forming a cumulative flow area. In this arrangement, the air accumulators 620, 630 serve as reservoirs that are kept nearly fully inflated by the bellows 200 as the plurality of apertures 640 supply a generally continuous release of airflow 300 towards the skin of the wearer. Preferably, the plurality of apertures 640 are oriented towards the crotch region on the wearer. For the embodiment shown in FIGS. 9a and 9b, the absorbent core 28 is narrower in width than the topsheet 24 and the backsheet 26 and centered relative thereto forming core free regions 55 along the longitudinal edges 50 of the diaper 20. The air accumulators 620, 630 extend along the core free regions 55 of the absorbent article from the front waist region 36, through the crotch region 37 and into the rear waist region 38.

The air accumulators 620, 630 can comprise inflatable chambers 622, 632. Inflatable chambers 622, 632 can be formed by peripherally joining two air accumulator chamber walls 624 and 634 with air accumulator wall 650 at seams 610. In FIG. 9b air accumulator wall 650 comprises a portion of the backsheet 26 which completes the enclosure of the inflatable chambers 622, 632. Alternatively, the air accumulator wall 650 can comprise a separate wall piece, such as a layer of thermoplastic film disposed intermediate the air accumulator walls 624 and 634 and the backsheet 26.

The air accumulator walls 624 and 634 of the inflatable chambers 622, 632 should be gas impermeable, and are preferably made from a material which is soft and flexible and more preferably, resilient. In one embodiment, one or both of the air accumulator walls 624 and 634 can be formed from an elastomeric or stretchable film. Suitable materials for air accumulator walls 624 and 634 include but are not limited to thermoplastic films, thermoplastic film/metal foil laminates, natural rubbers, and laminated films of natural rubber and synthetic thermoplastics. Suitable materials for air accumulator walls 624 and 634 include polyethylene films having a thickness between 0.000635 and 0.0127 centimeters (0.25 to 5.0 mils).

Suitable materials from which one or both of the air accumulator walls 624 and 634 can be made include materials from which the backsheet 42 can be formed, such as the Tredegar X8297 and the Clopay P-18-1401 films listed above. Other suitable materials from which one or both of the air accumulator walls 624 and 634 can be made include a polyethylene film available from Tredegar Industries designated C-8323.

The air accumulator walls 624 and 634 and wall 650 can be preformed, such as by vacuum forming. By way of example, air accumulator walls 624 and 634 can be vacuum formed to provide a generally semi-circular or rectangular cross-section upon inflation of chamber 622, 632. The air accumulator walls 624 and 634 can be joined at seams 610 by any suitable joining method such as heat/pressure sealing, adhesive bonding, ultrasonic bonding, or the like. Suitable seams 610 can be formed by heat sealing with a Vertrod Impulse Heat Sealing Unit, Model 12H, 500 watts, set at high pressure with a heat impulse power setting of 1.0 second. Such a heat sealing unit is manufactured by The Vertrod Corporation of Brooklyn, N.Y.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. An absorbent article having opposing longitudinal edges, a first end edge and a second end edge opposite the first end edge, a first waist region adjacent to the first end edge, a second waist region adjacent to the second end edge and a crotch region disposed between the first waist region and the second waist region, the absorbent article comprising:
   a backsheet;
   a topsheet joined coextensively with the backsheet;
   an absorbent core disposed intermediate the backsheet and the topsheet;
   a bellows disposed on the absorbent article, the bellows being repeatably deformable to force airflow through the absorbent article, the bellows expands and contracts utilizing biomechanical motion of the wearer drawing air into the bellows through at least one inlet port and expelling air out of the bellows through at least one outlet port; and
   at least one inflatable air accumulator attached to the at least one outlet port, the inflatable air accumulator having a plurality of apertures disposed on a body facing side thereof wherein the air accumulator provides a reservoir supplying a gradual, generally continuous airflow through the plurality of apertures.

2. The absorbent article according to claim 1 wherein the inflatable air accumulator extends from the front waist region, through at least a portion of the crotch region.

3. The absorbent article according to claim 1 wherein the absorbent core is narrower in width than the topsheet and the backsheet and centered relative thereto forming core free regions along the longitudinal edges of the absorbent article.

4. The absorbent article according to claim 3 wherein the outlet port comprises at least two apertures each having a separate inflatable air accumulator attached thereto, wherein the separate air accumulators extend along the core free regions of the absorbent article from the front waist region, through the crotch region and into the rear waist region.

5. An absorbent article comprising a bellows which is repeatably deformable to force airflow through the absorbent article in a controlled manner, wherein the bellows has a volume displacement rate ranging from about 1 in$^3$/minute to about 50 in$^3$/minute.

6. The absorbent article of claim 5 wherein the bellows further comprises a resilient element, wherein the resilient element comprises an opened cell foam.

* * * * *

UNITED STATES PATENT AND TRADEMARK OFFICE
CERTIFICATE OF CORRECTION

PATENT NO.     : 6,450,997 B1                                                   Page 1 of 1
DATED          : September 17, 2002
INVENTOR(S)    : Seitz et al.

It is certified that error appears in the above-identified patent and that said Letters Patent is hereby corrected as shown below:

<u>Title page, Item [54] and Column 1, line 1,</u>
Title "ARTICLES" after the word "ABSORBENT" should read -- ARTICLE --.

<u>Column 11,</u>
Line 4, "past" should read -- pant --.
Line 60, "thereof" should read -- thereof. --.

<u>Column 15,</u>
Line 17, "repeatably" should read -- repeatedly --.

<u>Column 19,</u>
Line 2, "repeatably" should read -- repeatedly --.

Signed and Sealed this

Twenty-fifth Day of February, 2003

JAMES E. ROGAN
*Director of the United States Patent and Trademark Office*